US006673816B1

(12) United States Patent
Esswein et al.

(10) Patent No.: US 6,673,816 B1
(45) Date of Patent: Jan. 6, 2004

(54) RHODANINE CARBOXYLIC ACID DERIVATIVES FOR THE TREATMENT AND PREVENTION OF METABOLIC BONE DISORDERS

(75) Inventors: Angelika Esswein, Birkenweg 4, D-64572 Büttleborn (DE); Wolfgang Schaefer, Mannheim (DE); Christos Tsaklakidis, Weinheim (DE); Konrad Honold, Suedstrasse 24, D-82377 Penzberg (DE); Klaus Kaluza, Bad Heilbrunn (DE)

(73) Assignees: Angelika Esswein (DE); Wolfgang Schafer (DE); Konrad Honold (DE)

( * ) Notice: Subject to any disclaimer, the term of this patent is extended or adjusted under 35 U.S.C. 154(b) by 0 days.

(21) Appl. No.: 09/787,917

(22) PCT Filed: Sep. 30, 1999

(86) PCT No.: PCT/EP99/07248

§ 371 (c)(1), (2), (4) Date: Jun. 21, 2001

(87) PCT Pub. No.: WO00/18747

PCT Pub. Date: Apr. 6, 2000

(30) Foreign Application Priority Data

Sep. 30, 1998 (EP) .............................. 98118493

(51) Int. Cl.[7] ................. A61K 31/426; A61K 31/427; C07D 277/36; C07D 417/06
(52) U.S. Cl. ................. 514/326; 514/369; 546/209; 548/183
(58) Field of Search ................. 548/183; 546/209; 514/369, 326

(56) References Cited

U.S. PATENT DOCUMENTS

| 4,777,259 A | * 10/1988 | Ogawa et al. ............... 548/183 |
| 5,143,927 A | 9/1992 | Boschelli et al. |
| 5,143,929 A | 9/1992 | Belliotti et al. |
| 5,747,517 A | 5/1998 | Panetta et al. |

FOREIGN PATENT DOCUMENTS

| DE | 43 18 550 | 12/1994 |
| EP | 0 045 165 | 3/1982 |
| EP | 0 047 109 | 3/1982 |
| EP | 0 237 138 | 9/1987 |
| EP | 0 291 007 | 11/1988 |
| EP | 0 343 643 | 11/1989 |
| EP | 0 391 644 | 10/1990 |
| EP | 0 425 109 | 5/1991 |
| EP | 0 434 394 | 6/1991 |
| EP | 0 587 377 | 3/1994 |
| EP | 0 677 517 | 10/1995 |
| EP | 691129 | * 1/1996 |
| WO | 96 26207 | 8/1996 |
| WO | 98 01445 | 1/1998 |

OTHER PUBLICATIONS

Turkevich et al., CA 72:121421, 1970.*

* cited by examiner

Primary Examiner—Laura L. Stockton
(74) Attorney, Agent, or Firm—Rothwell, Figg, Ernst & Manbeck

(57) ABSTRACT

Compounds of general formula (I), in which m is 0–8, q is a 0–8, a is 0–4, A signifies a single or double bond, $R_1$, $R_2$ signify hydrogen or lower alkyl and, when m signifies 2–8, $R_1$ and $R_2$ in the group $CR_1=CR_2$ can have various significances within the following sequence, $R_3$ signifies hydrogen or lower alkyl, X signifies hydrogen or $-(CH_2)_b-COR_4$ with b=0–4, Y signifies hydrogen, $-COR_4$, phenyl or indolyl residue $R_4$ signifies hydroxyl, lower alkoxy or the $NR_1R_2$ residue, W signifies an optionally mono- or polysubstituted saturated or unsaturated mono-, bi- or tricycle which can contain hetero atoms, as well physiologically compatible salts, esters, optically active forms, racemates, tautomers, and derivatives which can be metabolized in vivo to compounds of general formula (I).

(I)

$$W-[CH_2]_q-[CR_2=CR_1]_m \underset{R_3}{\overset{S}{\bigg|}} \text{rhodanine ring with } [CH_2]_a-Y \text{ and } X$$

3 Claims, No Drawings

RHODANINE CARBOXYLIC ACID DERIVATIVES FOR THE TREATMENT AND PREVENTION OF METABOLIC BONE DISORDERS

This application is a 371 of PCT/EP99/07248 filed Sep. 30, 1999.

The present invention is concerned with rhodanine carboxylic acid derivatives for the treatment and prevention of metabolic bone disorders, a process for their manufacture as well as medicaments which contain these compounds.

In healthy persons the synthesis and degradation processes in bones is almost in equilibrium, i.e. the activity of the osteoblasts and osteoclasts is balanced. However, if this equilibrium is disturbed in favour of the osteoclasts and/or to the detriment of the osteoblasts, this leads to a reduction in the bone mass and to a negative change in the bone structure and function.

Hitherto, bone resorption inhibitors such as oestrogens, calcitonin and biphosphonates have primarily been used for the treatment of metabolic bone disorders. The use of these substances is, however, limited and also does not show the desired effect in all cases. Compounds which have a stimulating activity on bone synthesis and in addition contribute to an increase in an already reduced bone mass are accordingly of especial significance for the treatment of metabolic bone disorders.

Compounds having the rhodanine carboxylic acid structural element are known as antidiabetics, cytostatics inflammation inhibitors and for the treatment of cardiovascular illnesses and bacterial infections.

The parathyroid hormone (PTH), a hormone from the parathyroid gland, is the natural ligand of the receptor and an important regulator for the maintenance of the calcium level in the body. PTH can stimulate bone formation or bone resorption. In this, it acts as a regulatory hormone on a series of enzymes, inter alia, on adenylate cyclase (cAMP synthesis) and on ornithine decarboxylase. PTH mobilizes calcium from bones in the case of calcium deficiency, reduces calcium excretion from the kidneys and simultaneously improves the resorption of calcium from the intestine by an increased synthesis of $1,25$—$(OH)_2D_3$. A normalization of the calcium level is achieved by the action on these target organs. On the other hand, the incorporation of calcium in bones is stimulated in the case of an elevated calcium level. This osteoanabolic activity of PTH and its fragments has been attributed to the activation of adenylate cyclase and of cAMP-dependent protein kinases (Rixon, R. Whitfield, J. et al JMBR 9 (8) 1179–89 (1994).

Surprisingly, it has now been found that rhodanine carboxylic acid derivatives of the present invention stimulate the PTH receptor-mediated cAMP formation. Compounds of the present invention are accordingly suitable for the broad treatment of metabolic bone disorders. They can be used primarily to good effect where the bone synthesis is disturbed, i.e. they are especially suitable for the treatment of osteopenic disorders of the skeletal system such as e.g. osteoporosis, inter alia, osteogenesis imperfecta as well as for the local assistance in bone regeneration and osteoinduction such as e.g. in orthopedic and maxillary medical indications, in fracture healing, osteosyntheses, pseudoarthroses and for the healing in of bone implants. However, having regard to these properties they also find use in the prophylaxis of osteoporosis.

By their influence on bone metabolism medicaments with the rhodanine carboxylic acid derivatives of the present invention as active substances furthermore form a basis for the local and systemic treatment of rheumatoid arthritis, osteoarthritis and degenerative arthrosis.

The object of the present invention are compounds of general formula (I),

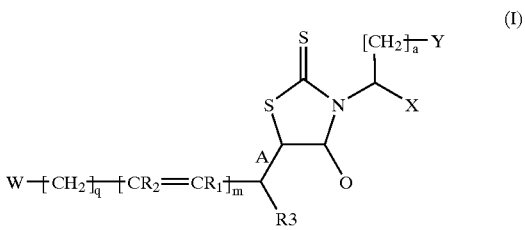

in which
m signifies a number between 0–8,
q signifies a number between 0–8
a signifies a number between 0–4
A signifies a single or double bond
$R_1$, $R_2$ signify hydrogen or lower alkyl, whereby $R_1$ and $R_2$ can be the same or different and, when m signifies 2–8, $R_1$ and $R_2$ in the group $CR_1$=$CR_2$ can have various significances within the following sequence
$R_3$ signifies hydrogen or lower alkyl
X signifies hydrogen or —$(CH_2)_b$—$COR_4$ with b=0–4
Y signifies hydrogen, —$COR_4$, phenyl or indolyl residue
$R_4$ signifies hydroxyl, lower alkoxy or the $NR_1R_2$ residue, whereby $R_1$ and $R_2$ can be the same or different
W signifies an optionally mono- or polysubstituted saturated or unsaturated mono-, bi- or tricycle which can contain one or more hetero atoms, As a rule, lower alkyl signifies linear or branched alkyl residues with one to six carbon atoms, preferably methyl, ethyl, propyl, i-propyl, butyl, t-butyl, pentyl, hexyl, particularly methyl.

Alkoxy groups signify a combination of a $C_1$–$C_{10}$-alkyl group in accordance with the above definition with an oxygen atom, e.g. methoxy, ethoxy, propoxy, isopropoxy, butoxy and pentoxy groups.

Under monocycle there are to be understood optionally mono- or polysubstituted, saturated or unsaturated ring systems with 3–8, preferably 3–7 carbon atoms, which optionally can be interrupted by one or more hetero atoms, such as nitrogen, oxygen or sulphur, especially the phenyl, pyridyl, pyrimidinyl, pyridazinyl, pyrazinyl, cyclopentyl, cyclohexyl, cyclohexenyl, cycloheptyl, morpholinyl, thiamorpholinyl, piperidinyl, piperazinyl, tetrahydrofuranyl, tetrahydropyranyl, furyl, thiophenyl, imidazolyl, thiazolyl, oxazolyl, isothiazolyl, isoxazolyl, 1,2,3-triazolyl or 1,2,4-triazolyl residue, as well as residues such as e.g. phenyl phenyl ether, diphenylmethane and biphenyl. Substituents are preferably lower alkyl, alkoxy, alkoxycarbonylalkyl, alkoxycarbonyl, acetylamino, alkoxydialkylamino, amino, dialkylamino, benzyl, benzyloxy, benzyloxybenzyloxy, carboxyl, chlorophenylsulphanyl, dioxymethylene, mercaptoalkyl, nitro, phenoxy, styryl and halogen.

In the case of the bicycle set forth under W, this is preferably a residue such as the naphthyl, tetrahydronaphthyl, decalinyl, quinolinyl, chromane, chromene, isoquinolinyl, tetrahydroquinolinyl, tetrahydroisoquinolinyl, indolyl, benzimidazolyl, indazolyl, oxindolyl, benzofuranyl, benzothiophenyl, benzochiazolyl, benzoxazolyl or purinyl residue, especially the indolyl, naphthyl, benzimidazolyl, quinolinyl, tetrahydroquinolinyl benzothiophenyl and benzofuranyl residue, which optionally can be mono- or polysubstituted. Substituents are preferably lower alkyl, alkoxy, alkoxycarbonylalkyl, alkoxycarbonyl, acetylamino, alkoxydialkylamino, amino, dialkylamino, benzyl, benzyloxy, benzyloxybenzyloxy, carboxyl, chlorophenylsulphanyl, dioxymethylene, mercaptoalkyl, nitro, phenoxy, styryl and halogen.

In the case of the tricycle set forth under W, this is preferably a residue such as the anthracene, fluorene, dibenzofuran or carbazole.

Compounds of formula I wherein W is phenyl or indolyl, m and g are both 0, $R_3$ is hydrogen and A is a double bond are disclosed e.g. in EP-A-0677 and EP-A-0587377, however for the treatment of Alzheimer's disease or as hypoglycemic agents.

Therefore subject of the present invention are also new compounds of formula I

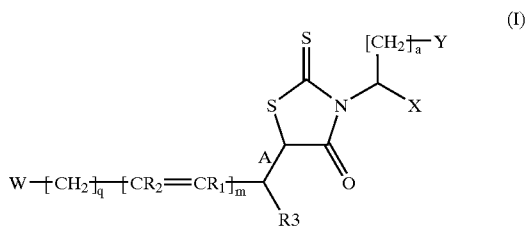

(I)

in which
  m signifies a number between 0–8,
  q signifies a number between 0–8
  a signifies a number between 0–4
  A signifies a single or double bond
  $R_1$, $R_2$ signify hydrogen or lower alkyl, whereby $R_1$ and $R_2$ can be the same or different and, when m signifies 2–8, $R_1$ and $R_2$ in the group $CR_1=CR_2$ can have various significances within the following sequence
  $R_3$ signifies hydrogen or lower alkyl
  X signifies hydrogen or —$(CH_2)_b$—$COR_4$ with b=0–4
  Y signifies hydrogen, —$COR_4$, phenyl or indolyl residue
  $R_4$ signifies hydroxyl, lower alkoxy or the $NR_1R_2$ residue, whereby $R_1$ and $R_2$ can be the same or different
  W signifies an optionally mono- or polysubstituted saturated or unsaturated mono-, bi- or tricycle which can contain one or more hetero atoms,
  whereas W is not phenyl or indolyl, if m and g are both 0, $R_3$ is hydrogen and A is a double bond, as well as their physiologically compatible salts, esters, optically active forms, racemates, tautomers, as well as derivatives which can be metabolized in vivo to compounds of general formula (I), as well as the use of these compounds for the production of medicaments.

Preferred are compounds of general formula I in which m signifies a number between 0 and 4, q signifes the number 0 or 1, a signifies a number of 0 to 4, A signifies a double bond, $R_{1,2}$ signify hydrogen or methyl, X signifies hydrogen or —$(CH_2)_b$—$COR_4$ with b=0–2 and $R_4$ equals hydroxyl, methoxy or $NR_1R_2$, Y signifies hydrogen or $COR_4$, the phenyl or indolyl residue, $R_3$ signifies hydrogen or methyl and W signifies an optionally mono- or polysubstituted benzothiophene, phenyl, benzofuran, thiophene, naphthalene, piperidine, cyclohexenyl or biphenyl residue.

The manufacture of the compounds of general formula (I) is possible according to methods known per se. Examples of the methods of synthesis are set forth in Schemes 1 and 2; whereby R signifies the group:

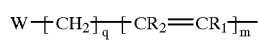

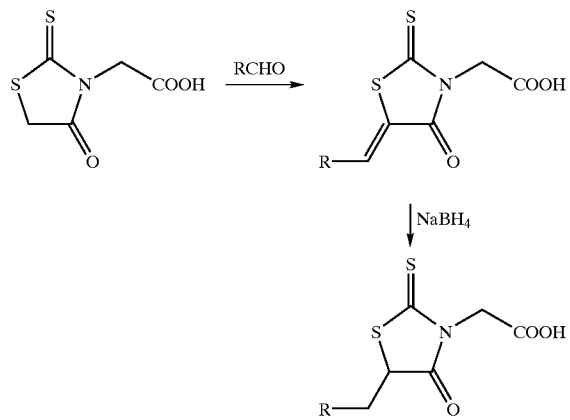

Scheme 1
(Lit.: Chem. Pharm. Bull. 38 1911-19 (1990); 40 907-11 (1992))

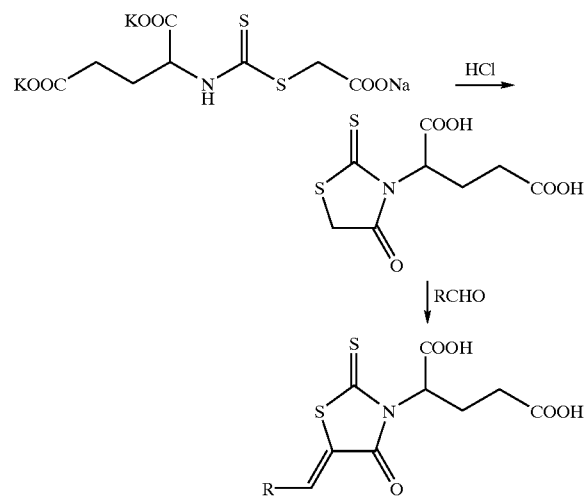

Scheme 2
(Lit: Chem. Heterocycl. Compd. EN 3 528-30 (1967))

The rhodanine carboxylic acids and aldehydes used as starting materials are either commercially available, known or can be prepared analogously to the generally known processes.

Compounds of formula (I) can be administered (sic) in liquid, solid or aerosol form orally, enterally, parenterally, topically, nasally, pulmonary or rectally in all usual non-toxic pharmaceutically acceptable carrier materials, adjuvants and additives. The compounds of formula (I) can also be applied locally to/in the bones (optionally with surgical intervention). The term parenteral embraces subcutaneous, intravenous and intramuscular delivery or infusions. Oral administration forms can be e.g. tablets, capsules, dragees, syrups, solutions, suspensions, emulsions, elixirs etc., which can contain one or more additives from the following groups, such as flavourings, sweeteners, colouring agents and preservatives. Oral administration forms contain the active ingredient together with non-toxic, pharmaceutically acceptable carrier materials which are suitable for the production of tablets, capsules, dragees etc., such as e.g., calcium carbonate, sodium carbonate, lactose, calcium phosphate or sodium phosphate; starch, mannitol, methylcellulose, talc, highly dispersible silicic acids, high molecular fatty acids (such as stearic acid), groundnut oil, olive oil, paraffin, miglyol, gelatine, agar-agar, magnesium stearate, beeswax, cetyl alcohol, lecithin, glycerol, animal and vegetable fats, solid high molecular polymers (such as polyethylene glycol). Tablets, capsules, dragees etc. can be provided with an appropriate coating, e.g. glyceryl monostearate or glyceryl distearate, in order to prevent undesired side effects in the gastrointestinal tract or to give a longer duration of action by the delayed absorption in the gastrointestinal tract. As the injection medium there are preferably used sterile injectable aqueous or oily solutions or suspensions which contain the usual additives such as stabilizers and solubilizers. Such additives can be e.g. water, isotonic saline, 1,3-butanediol, fatty acids (such as oleic acid), mono- and diglycerides or miglyol. For rectal use there can be used all suitable non-irritating additives which are solid at normal temperatures and liquid at rectal temperatures, such as e.g. cocoa butter and polyethylene glycol. Pharmaceutically usual carrier media are used for application as aerosols. Creams, tinctures, gels, solutions or suspensions etc. with the pharmaceutically usual additives are used for external application. The dosage can depend n a variety of factors such as mode of administration, species, age and/or individual condition. The doses to be administered daily or at intervals lie at 1–1000 mg/individual, preferably at 10–250 mg/individual, and can be taken at one time or divided over several times.

The compounds of formula (I) can also be applied locally to/in the bones (optionally with surgical intervention). The application directly to/in the bones (optionally with surgical intervention) can be effected locally or carrier-bonded either in solution or suspension, conveniently by infusion or injection. Carrier-bonded compounds of formula (I) can be administered, for example, as gels, pastes, solids or as a coating on implants.

Biocompatible and preferably biodegradable materials are used as the carrier. Preferably, the materials themselves also induce wound healing or osteogenesis.

For local application it is preferred that the compounds of formula (I) are imbedded in polymer gels or films in order to immobilize them and to apply these preparations directly on the site of the bone to be treated. Such polymer-based gels or films consist, for example, of glycerine, methylcellulose, hyaluronic acid, polyethylene oxides and/ or poloxamers. Also suitable are collagen, gelatines and alginates and are described, for example, in WO 93/00050 and WO 93/20859. Further polymers are polylactic acid (PLA) and copolymers of lactic acid and glycolic acid (PLPG) (Hollinger el al., J. Biomed. Mater. Res. 17 71–82 (1983)) as well as the bone derivative "Demineralized Bone Matrix" (DBM) (Guterman et al. Kollagen Rel. Res. 8 419–4319 (1988). Also suitable are polymers as are used, for example, for the adsorption of TGFβ and which are described in EP-A 0 616 814 and EP-A-0 567 391 and synthetic bone matrices in accordance with WO 91/18558.

Likewise suitable as carriers for the compounds of formula (I) are materials which are usually used for the implantation of bone substitutes or otherwise of therapeutically active substances. Such carriers are based, for example, on calcium sulphate, tricalcium phosphate, hydroxylapatite (sic) and its biodegradable derivatives and polyanhydrides. Apart from these biodegradable carriers there are also suitable carriers which are not biodegradable, but which are biocompatible. Such carriers are, for example, sintered hydroxylapatite, bioglass, aluminates or other ceramic materials (e.g. calcium aluminium phosphate). These materials are preferably used in combination with the biodegradable materials, such as especially polylactic acid, hydroxylapatite, collagen or tricalcium phosphate. Further non-degradable carriers are described, for example, in U.S. Pat. No. 4,164,560.

It is especially preferred to use a carrier which liberates the compounds of formula (I) continuously at the target site. Especially suitable for this are e.g. "slow release pellets" from Innovative Research of America, Toledo, Ohio, USA. Pellets which release the compounds of formula (I) over several days, preferably up to 100 days with a daily dosage of 1–10 mg/kg per day, are especially preferred.

Preferred in the scope of the present invention are, apart form the compounds named in the Examples and compounds derivable by a combination of all of the significances of the substituents set forth in the claims, the following derivatives as well as their physiologically compatible salts, esters, optically active forms, racemates, tautomers as well as derivatives which can be metabolized in vivo to compounds of general formula (I), as well as the use of these compounds for the production of medicaments.

Preferred Compounds (PC)

1. [5-(9H-Fluoren-2-ylmethylene)-4-oxo-2-thioxo-thiazolidin-3-yl]-acetic acid
2. (4-Oxo-5-phenanthren-9-ylmethyl-2-thioxo-thiazolidin-3-yl)-acetic acid
3. [5-(3-Anthracen-9-yl-allylidene)-4-oxo-2-thioxo-thiazolidin-3-yl]-acetic acid
4. 3-[5-(10-Methyl-anthracen-9-ylmethylene)-4-oxo-2-thioxo-thiazolidin-3-yl]-propionic acid
5. 3-[5-(5-Furan-2-yl-penta-2,4-dienylidene)-4-oxo-2-thioxo-thiazolidin-3-yl]-propionic acid
6. 2-(5-Benzylidene-4-oxo-2-thioxo-thiazolidin-3-yl)-succinic acid
7. 2-[5-(2-Methoxy-benzylidene)-4-oxo-2-thioxo-thiazolidin-3-yl]-pentane-dicarboxylic acid
8. [4-Oxo-2-thioxo-5-(2,3,4-trimethoxy-benzyl)-thiazolidin-3-yl]-acetic acid
9. {5-[3-(2,4-Dimethoxy-phenyl)-allylidene]-4-oxo-2-thioxo-thiazolidin-3-yl}-acetic acid
10. 3-[4-Oxo-2-thioxo-5-(2,4,5-trimethoxy-benzylidene)-thiazolidin-3-yl]-propionic acid
11. 3-{4-Oxo-2-thioxo-5-[3-(2,4,6-trimethoxy-phenyl)-allylidene]-thiazolidin-3-yl}-propionic acid
12. 2-[5-(2,5-Dimethoxy-benzylidene)-4-oxo-2-thioxo-thiazolidin-3-yl]-succinic acid
13. 2-[5-(2-Ethoxy-benzylidene)-4-oxo-2-thioxo-thiazolidin-3-yl]-pentanedicarboxylic acid
14. [5-(2-Hydroxy-3-methoxy-benzyl)-4-oxo-2-thioxo-thiazolidin-3-yl]-acetic acid
15. {5-[3-(3-Ethoxy-2-hydroxy-phenyl)-allylidene]-4-oxo-2-thioxo-thiazolidin-3-yl}-acetic acid
16. 3-[5-(2,3-Dihydroxy-benzylidene)-4-oxo-2-thioxo-thiazolidin-3-yl]-propionic acid
17. 3-{4-Oxo-2-thioxo-5-[3-(2,3,4-trihydroxy-phenyl)-allylidene]-thiazolidin-3-yl}-propionic acid
18. 2-[5-(4-Diethylamino-2-hydroxy-benzylidene)-4-oxo-2-thioxo-thiazolidin-3-yl]-succinic acid
19. 2-[5-(2-Hydroxy-4-methoxy-benzylidene)-4-oxo-2-thioxo-thiazolidin-3-yl]-pentanedicarboxylic acid
20. [5-(2-Hydroxy-5-methoxy-benzyl)-4-oxo-2-thioxo-thiazolidin-3-yl]-acetic acid
21. {5-[3-(2,5-Dihydroxy-phenyl)-allylidene]-4-oxo-2-thioxo-thiazolidin-3-yl}-acetic acid 22. 3-[5-(2-Methyl-benzylidene)-4-oxo-2-thioxo-thiazolidin-3-yl]-propionic acid
23. 3-{5-[3-(4-Methoxy-2,3-dimethyl-phenyl)-allylidene]-4-oxo-2-thioxo-thiazolidin-3-yl}-propionic acid
24. 2-[4-Oxo-2-thioxo-5-(2,4,6-trimethyl-benzylidene)-thiazolidin-3-yl]-succinic acid
25. 2-[5-(2,5-Dimethyl-benzylidene)-4-oxo-2-thioxo-thiazolidin-3-yl]-pentane-dicarboxylic acid
26. {5-[3-(4-Methoxy-phenoxy)-benzyl]-4-oxo-2-thioxo-thiazolidin-3-yl}-acetic acid
27. (5-{3-[3-(4-tert-Butyl-phenoxy)-phenyl]-allylidene}-4-oxo-2-thioxo-thiazolidin-3-yl)-acetic acid
28. 3-[4-Oxo-2-thioxo-5-(3-#p!-tolyloxy-benzylidene)-thiazolidin-3-yl]-propionic acid
29. 3-{5-[3-(3-Methoxy-phenyl)-allylidene]-4-oxo-2-thioxo-thiazolidin-3-yl}-propionic acid
30. 2-[5-(3,4-Dimethoxy-benzylidene)-4-oxo-2-thioxo-thiazolidin-3-yl]-succinic acid
31. 2-[4-Oxo-2-thioxo-5-(3,4,5-trimethoxy-benzylidene)-thiazolidin-3-yl]-pentanedicarboxylic acid
32. [5-(3,5-Dimethoxy-benzyl)-4-oxo-2-thioxo-thiazolidin-3-yl]-acetic acid
33. {5-[3-(3-Benzyloxy-phenyl)-allylidene]-4-oxo-2-thioxo-thiazolidin-3-yl}-acetic acid
34. 3-[5-(3-Hydroxy-benzylidene)-4-oxo-2-thioxo-thiazolidin-3-yl]-propionic acid
35. 3-{5-[3-(3-Hydroxy-4-methoxy-phenyl)-allylidene]-4-oxo-2-thioxo-thiazolidin-3-yl}-propionic acid
36. 2-[5-(3,4-Dihydroxy-benzylidene)-4-oxo-2-thioxo-thiazolidin-3-yl]-succinic acid
37. 2-[5-(3-Methyl-benzylidene)-4-oxo-2-thioxo-thiazolidin-3-yl]-pentanedicarboxylic acid
38. [5-(4-Dimethylamino-benzyl)-4-oxo-2-thioxo-thiazolidin-3-yl]-acetic acid
39. {5-[3-(4-Diethylamino-phenyl)-allylidene]-4-oxo-2-thioxo-thiazolidin-3-yl}-acetic acid
40. 3-[4-Oxo-5-(4-phenoxy-benzylidene)-2-thioxo-thiazolidin-3-yl]-propionic acid
41. 3-{5-[3-(4-Methoxy-phenyl)-allylidene]-4-oxo-2-thioxo-thiazolidin-3-yl}-propionic acid
42. 2-[5-(3-Benzyloxy-4-methoxy-benzylidene)-4-oxo-2-thioxo-thiazolidin-3-yl]-succinic acid
43. 2-[5-(4-Benzyloxy-benzylidene)-4-oxo-2-thioxo-thiazolidin-3-yl]-pentane-dicarboxylic acid
44. [5-(4-Butoxy-benzyl)-4-oxo-2-thioxo-thiazolidin-3-yl]-acetic acid
45. [5-(3-Naphthalen-1-yl-allylidene)-4-oxo-2-thioxo-thiazolidin-3-yl]-acetic acid
46. 3-[5-(2-Methoxy-naphthalen-1-ylmethylene)-4-oxo-2-thioxo-thiazolidin-3-yl]-propionic acid
47. 3-{5-[3-(2-Hydroxy-naphthalen-1-yl)-allylidene]-4-oxo-2-thioxo-thiazolidin-3-yl}-propionic acid
48. 2-[5-(4-Methoxy-naphthalen-1-ylmethylene)-4-oxo-2-thioxo-thiazolidin-3-yl]-succinic acid
49. 2-(5-Naphthalen-2-ylmethylene-4-oxo-2-thioxo-thiazolidin-3-yl)-pentane-dicarboxylic acid
50. [5-(9-Ethyl-9H-carbazol-3-ylmethyl)-4-oxo-2-thioxo-thiazolidin-3-yl]-acetic acid
51. {5-[3-(1H-Indol-3-yl)-allylidene]-4-oxo-2-thioxo-thiazolidin-3-yl}-acetic acid
52. 3-[5-(5-Methoxy-1H-indol-3-ylmethylene)-4-oxo-2-thioxo-thiazolidin-3-yl]-propionic acid
53. 3-[5-(3-Benzo[1,3]dioxol-5-yl-allylidene)-4-oxo-2-thioxo-thiazolidin-3-yl]-propionic acid
54. 2-[5-(4-Hydroxy-benzylidene)-4-oxo-2-thioxo-thiazolidin-3-yl]-pentane-dicarboxylic acid
55. [5-(4-Hydroxy-3,5-dimethoxy-benzyl)-4-oxo-2-thioxo-thiazolidin-3-yl]-acetic acid
56. {5-[3-(3-Ethoxy-4-hydroxy-phenyl)-allylidene]-4-oxo-2-thioxo-thiazolidin-3-yl}-acetic acid
57. 3-[5-(4-Hydroxy-3,3-dimethyl-benzylidene)-4-oxo-2-thioxo-thiazolidin-3-yl]-propionic acid
58. 3-[5-(3-Biphenyl-4-yl-allylidene)-4-oxo-2-thioxo-thiazolidin-3-yl]-propionic acid
59. 2-[5-(4-Isopropyl-benzylidene)-4-oxo-2-thioxo-thiazolidin-3-yl]-pentane-dicarboxylic acid
60. [5-(4-Ethyl-benzyl)-4-oxo-2-thioxo-thiazolidin-3-yl]-acetic acid
61. [5-(4,4-Diphenyl-but-2-enylidene)-4-oxo-2-thioxo-thiazolidin-3-yl]-acetic acid
62. 3-[4-Oxo-5-(2-phenyl-propylidene)-2-thioxo-thiazolidin-3-yl]-propionic acid
63. 3-[5-(4-Methyl-5-phenyl-penta-2,4-dienylidene)-4-oxo-2-thioxo-thiazolidin-3-yl]-propionic acid
64. 2-[5-(2-Hexyl-3-phenyl-allylidene)-4-oxo-2-thioxo-thiazolidin-3-yl]-pentane-dicarboxylic acid
65. [4-Oxo-5-(5-phenyl-penta-2,4-dienylidene)-2-thioxo-thiazolidin-3-yl]-acetic acid
66. 3-{5-[3-(2-Methoxy-phenyl)-allylidene]-4-oxo-2-thioxo-thiazolidin-3-yl}-propionic acid
67. 3-{5-[5-(4-Dimethylamino-phenyl)-penta-2,4-dienylidene]-4-oxo-2-thioxo-thiazolidin-3-yl}-propionic acid
68. [5-(3-Ethoxy-4-methoxy-benzyl)-4-oxo-2-thioxo-thiazolidin-3-yl]-acetic acid
69. {5-[3-(4-Diethoxymethyl-phenyl)-allylidene]-4-oxo-2-thioxo-thiazolidin-3-yl}-acetic acid
70. 3-[5-(4-Dimethylamino-naphthalen-1-ylmethylene)-4-oxo-2-thioxo-thiazolidin-3-yl]-propionic acid
71. 2-[5-(2,4-Dimethoxy-3-methyl-benzylidene)-4-oxo-2-thioxo-thiazolidin-3-yl]-pentanedicarboxylic acid
72. [4-Oxo-5-(4-styryl-benzylidene)-2-thioxo-thiazolidin-3-yl]-acetic acid
73. {5-[4-(3-Dimethylamino-propoxy)-benzyl]-4-oxo-2-thioxo-thiazolidin-3-yl}-acetic acid
74. {5-[3-(2,4-Dihydroxy-phenyl)-allylidene]-4-oxo-2-thioxo-thiazolidin-3-yl}-acetic acid
75. 3-[5-(2-Methyl-1H-indol-3-ylmethylene)-4-oxo-2-thioxo-thiazolidin-3-yl]-propionic acid
76. 3-{5-[3-(4-Hydroxy-3-methyl-phenyl)-allylidene]-4-oxo-2-thioxo-thiazolidin-3-yl}-propionic acid
77. 2-[5-(2-Hexyloxy-benzylidene)-4-oxo-2-thioxo-thiazolidin-3-yl]-pentane-dicarboxylic acid
78. [4-Oxo-5-(4-propoxy-benzyl)-2-thioxo-thiazolidin-3-yl]-acetic acid
79. {4-Oxo-5-[3-(4-pentyloxy-phenyl)-allylidene]-2-thioxo-thiazolidin-3-yl}-acetic acid
80. 3-[5-(4-Octyloxy-benzylidene)-4-oxo-2-thioxo-thiazolidin-3-yl]-propionic acid
81. 3-{5-[3-(5-Benzyloxy-1H-indol-3-yl)-allylidene]-4-oxo-2-thioxo-thiazolidin-3-yl}-propionic acid
82. 2-(5-Benzofuran-2-ylmethylene-4-oxo-2-thioxo-thiazolidin-3-yl)-pentane-dicarboxylic acid
83. [4-Oxo-5-(2,3,4,5,6-pentamethyl-benzyl)-2-thioxo-thiazolidin-3-yl]-acetic acid
84. {5-[3-(2-Benzyloxy-phenyl)-allylidene]-4-oxo-2-thioxo-thiazolidin-3-yl}-acetic acid
85. 3-[4-Oxo-2-thioxo-5-(2,3,4-trimethoxy-6-methyl-benzylidene)-thiazolidin-3-yl]-propionic acid
86. 3-{5-[3-(3-Ethoxy-phenyl)-allylidene]-4-oxo-2-thioxo-thiazolidin-3-yl}-propionic acid
87. 2-[5-(3,4-Dihydroxy-5-methoxy-benzylidene)-4-oxo-2-thioxo-thiazolidin-3-yl]-pentanedicarboxylic acid
88. [5-(3,4-Dimethyl-benzyl)-4-oxo-2-thioxo-thiazolidin-3-yl]-acetic acid 89. [5-[3-(4-Ethoxy-3-methoxy-phenyl)-allylidene]-4-oxo-2-thioxo-thiazolidin-3-yl]-acetic acid
90. 3-[5-(4-Hexyloxy-benzylidene)-4-oxo-2-thioxo-thiazolidin-3-yl]-propionic acid
91. 3-{5-[3-(4-Heptyloxy-phenyl)-allylidene]-4-oxo-2-thioxo-thiazolidin-3-yl}-propionic acid
92. 2-(5-Benzo[1,3]dioxol-4-ylmethylene-4-oxo-2-thioxo-thiazolidin-3-yl)-pentanedicarboxylic acid
93. [4-Oxo-2-thioxo-5-(2,4,5-trimethyl-benzyl)-thiazolidin-3-yl]-acetic acid
94. {5-[3-(4-Decyloxy-phenyl)-allylidene]-4-oxo-2-thioxo-thiazolidin-3-yl}-acetic acid
95. 3-{5-[3-(4-tert-Butyl-phenyl)-allylidene]-4-oxo-2-thioxo-thiazolidin-3-yl}-propionic acid
96. {5-[3-(4-Amino-phenyl)-allylidene]-4-oxo-2-thioxo-thiazolidin-3-yl}-acetic acid
97. 3-[5-(2-tert-Butylsulphanyl-benzylidene)-4-oxo-2-thioxo-thiazolidin-3-yl]-propionic acid
98. 3-{5-[3-(4-Butyl-phenyl)-allylidene]-4-oxo-2-thioxo-thiazolidin-3-yl}-propionic acid
99. 2-[5-(4-tert-Butoxy-benzylidene)-4-oxo-2-thioxo-thiazolidin-3-yl]-pentane-dicarboxylic acid
100. [4-Oxo-5-(4-propyl-benzylidene)-2-thioxo-thiazolidin-3-yl]-acetic acid
101. [5-(4-Hexyl-benzyl)-4-oxo-2-thioxo-thiazolidin-3-yl]-acetic acid
102. {5-[3-(4-Octyl-phenyl)-allylidene]-4-oxo-2-thioxo-thiazolidin-3-yl}-acetic acid
103. 3-[5-(4-Dodecyloxy-benzylidene)-4-oxo-2-thioxo-thiazolidin-3-yl]-propionic acid
104. 3-{4-Oxo-5-[3-(4-pentyl-phenyl)-allylidene]-2-thioxo-thiazolidin-3-yl}-propionic acid
105. 2-[5-(3-Amino-benzylidene)-4-oxo-2-thioxo-thiazolidin-3-yl]-pentane-dicarboxylic acid
106. [5-(7-Methyl-1H-indol-3-ylmethyl)-4-oxo-2-thioxo-thiazolidin-3-yl]-acetic acid
107. 3-[4-Oxo-2-thioxo-5-(2-p-tolyl-ethylidene)-thiazolidin-3-yl]-propionic acid
108. 3-{5-[3-(3,5-Dimethyl-1-phenyl-1H-pyrazol-4-yl)-allylidene]-4-oxo-2-thioxo-thiazolidin-3-yl}-propionic acid
109. [5-(4-Hydroxy-2-methoxy-benzyl)-4-oxo-2-thioxo-thiazolidin-3-yl]-acetic acid
110. {5-[3-(2,2-Dimethyl-chroman-6-yl)-allylidene]-4-oxo-2-thioxo-thiazolidin-3-yl}-acetic acid
111. 3-[5-(4-Isopropoxy-benzylidene)-4-oxo-2-thioxo-thiazolidin-3-yl]-propionic acid
112. 2-[5-(4-Methyl-naphthalen-1-ylmethylene)-4-oxo-2-thioxo-thiazolidin-3-yl]-pentanedicarboxylic acid
113. {5-[3-(2,3-Dihydro-benzofuran-5-yl)-allylidene]-4-oxo-2-thioxo-thiazolidin-3-yl}-acetic acid
114. 3-(4-Oxo-5-quinolin-2-ylmethylene-2-thioxo-thiazolidin-3-yl)-propionic acid
115. 3-{5-[5-(4-Diethylamino-phenyl)-penta-2,4-dienylidene]-4-oxo-2-thioxo-thiazolidin-3-yl}-propionic acid
116. 2-[5-(4-Isobutyl-benzylidene)-4-oxo-2-thioxo-thiazolidin-3-yl]-pentane-dicarboxylic acid
117. [5-(6-Methoxy-naphthalen-2-ylmethyl)-4-oxo-2-thioxo-thiazolidin-3-yl]-acetic acid
118. {5-[3-(3,5-Dimethyl-phenyl)-allylidene]-4-oxo-2-thioxo-thiazolidin-3-yl}-acetic acid
119. 3-[5-(1-Hydroxy-naphthalen-2-ylmethylene)-4-oxo-2-thioxo-thiazolidin-3-yl]-propionic acid
120. [5-(4-Octadecyloxy-benzyl)-4-oxo-2-thioxo-thiazolidin-3-yl]-acetic acid
121. {5-[3-(4-Diphenylamino-phenyl)-allylidene]-4-oxo-2-thioxo-thiazolidin-3-yl}-acetic acid
122. 3-[4-Oxo-2-thioxo-5-(3,4,5-trihydroxy-benzylidene)-thiazolidin-3-yl]-propionic acid
123. 3-{5-[3-(4-Dimethylamino-2-methoxy-phenyl)-allylidene]-4-oxo-2-thioxo-thiazolidin-3-yl}-propionic acid
124. {5-[2-(2-Hydroxy-ethoxy)-benzyl]-4-oxo-2-thioxo-thiazolidin-3-yl}-acetic acid
125. (5-{3-[4-(2-Hydroxy-ethoxy)-phenyl]-allylidene}-4-oxo-2-thioxo-thiazolidin-3-yl)-acetic acid
126. 3-[5-(2-Benzyloxy-ethylidene)-4-oxo-2-thioxo-thiazolidin-3-yl]-propionic acid
127. 3-{5-[3-(4-tert-Butoxycarbonyloxy-3-methoxy-phenyl)-allylidene]-4-oxo-2-thioxo-thiazolidin-3-yl}-propionic acid
128. 2-[5-(2,4-Diethoxy-3-methyl-benzylidene)-4-oxo-2-thioxo-thiazolidin-3-yl]-pentanedicarboxylic acid
129. [5-(2-Benzyloxy-3-methoxy-benzyl)-4-oxo-2-thioxo-thiazolidin-3-yl]-acetic acid
130. {5-[3-(4-Methanesulphonyl-phenyl)-allylidene]-4-oxo-2-thioxo-thiazolidin-3-yl}-acetic acid
131. 3-[5-(2-Hydroxy-5-methyl-benzylidene)-4-oxo-2-thioxo-thiazolidin-3-yl]-propionic acid
132. (4-Oxo-5-thiophen-2-ylmethyl-2-thioxo-thiazolidin-3-yl)-acetic acid
133. [5-(5-Naphthalen-2-yl-penta-2,4-dienylidene)-4-oxo-2-thioxo-thiazolidin-3-yl]-acetic acid
134. 3-[4-Oxo-5-(3-thiophen-2-yl-allylidene)-2-thioxo-thiazolidin-3-yl]-propionic acid
135. 3-{5-[3-(2-[1,3]Dioxolan-2-yl-6-fluoro-phenyl)-allylidene]-4-oxo-2-thioxo-thiazolidin-3-yl}-propionic acid
136. 2-[5-(3-tert-Butyl-4-hydroxy-benzylidene)-4-oxo-2-thioxo-thiazolidin-3-yl]-pentanedicarboxylic acid
137. [5-(4-Benzyl-benzyl)-4-oxo-2-thioxo-thiazolidin-3-yl]-acetic acid 138. {5-[5,9-Dimethyl-11-(2,6,6-trimethyl-cyclohex-1-enyl)-undeca-2,4,6,8,10-pentaenylidene]-4-oxo-2-thioxo-thiazolidin-3-yl}-acetic acid
139. 3-[4-Oxo-5-(1H-pyrrol-2-ylmethylene)-2-thioxo-thiazolidin-3-yl]-propionic acid
140. 3-[5-(3-Furan-2-yl-allylidene)-4-oxo-2-thioxo-thiazolidin-3-yl]-propionic acid
141. 2-{5-[3-(5,6-Diethoxy-benzo[b]thiophen-2-yl)-allylidene]-4-oxo-2-thioxo-thiazolidin-3-yl}-pentanedicarboxylic acid
142. (4-Oxo-5-pyridin-2-ylmethylene-2-thioxo-thiazolidin-3-yl)-acetic acid
143. [5-(1-Methyl-1H-pyrrol-3-ylmethyl)-4-oxo-2-thioxo-thiazolidin-3-yl]-acetic acid
144. {5-[3-(2-Hydroxy-4,6-dimethoxy-phenyl)-allylidene]-4-oxo-2-thioxo-thiazolidin-3-yl}-acetic acid
145. 3-[5-(4-Benzyloxy-2-hydroxy-benzylidene)-4-oxo-2-thioxo-thiazolidin-3-yl]-propionic acid
146. 3-{5-[3-(5-Benzyloxy-2-hydroxy-phenyl)-allylidene]-4-oxo-2-thioxo-thiazolidin-3-yl}-propionic acid
147. 2-{5-[4-(Benzo[1,3]dioxol-5-ylmethoxy)-benzylidene]-4-oxo-2-thioxo-thiazolidin-3-yl}-pentanedicarboxylic acid
148. [5-(4-Benzyloxy-3,5-dihydroxy-benzyl)-4-oxo-2-thioxo-thiazolidin-3-yl]-acetic acid
149. {5-[3-(2,5-Bis-benzyloxy-phenyl)-allylidene]-4-oxo-2-thioxo-thiazolidin-3-yl}-acetic acid
150. 3-[5-(4-Benzyloxy-3,5-dimethyl-benzylidene)-4-oxo-2-thioxo-thiazolidin-3-yl]-propionic acid
151. 3-[5-(3-Cyclohexyl-allylidene)-4-oxo-2-thioxo-thiazolidin-3-yl]-propionic acid
152. 2-{5-[3-Methyl-5-(2,6,6-trimethyl-cyclohex-1-enyl)-penta-2,4-dienylidene]-4-oxo-2-thioxo-thiazolidin-3-yl}-pentanedicarboxylic acid 153. [5-(3,4-Diethoxy-2,5-dimethyl-benzyl)-4-oxo-2-thioxo-thiazolidin-3-yl]-acetic acid
154. {5-[5-(3,4-Diethoxy-2,5-dimethyl-phenyl)-penta-2,4-dienylidene]-4-oxo-2-thioxo-thiazolidin-3-yl}-acetic acid
155. [5-(2-Carboxymethoxy-benzylidene)-4-oxo-2-thioxo-thiazolidin-3-yl]-propionic acid
156. 2-{3-[3-(2-Carboxy-ethyl)-4-oxo-2-thioxo-thiazolidin-5-yliden]-propenyl}-benzoic acid
157. 2-[5-(4-Acetoxy-benzylidene)-4-oxo-2-thioxo-thiazolidin-3-yl]-pentane-dicarboxylic acid
158. Methyl 4-(3-carboxymethyl-4-oxo-2-thioxo-thiazolidin-5-ylmethyl)-benzoate
159. 4-[3-(3-Carboxymethyl-4-oxo-2-thioxo-thiazolidin-5-yliden)-propenyl]-benzoic acid
160. 3-{4-[3-(2-Carboxy-ethyl)-4-oxo-2-thioxo-thiazolidin-5-ylidenmethyl]-phenyl}-acrylic acid
161. 3-{4-Oxo-5-[3-(4-oxo-4H-chromen-3-yl)-allylidene]-2-thioxo-thiazolidin-3-yl}-propionic acid
162. 2-[5-(4-Acetoxy-3,5-dimethoxy-benzylidene)-4-oxo-2-thioxo-thiazolidin-3-yl]-pentanedicarboxylic acid
163. 3-(3-Carboxymethyl-4-oxo-2-thioxo-thiazolidin-5-ylmethyl)-benzoic acid
164. 4-[3-(3-Carboxymethyl-4-oxo-2-thioxo-thiazolidin-5-yliden)-propenyl]-phenyl propionate
165. 3-[5-(5,7-Dimethyl-4-oxo-4H-chromen-3-ylmethylene)-4-oxo-2-thioxo-thiazolidin-3-yl]-propionic acid
166. 3-{5-[3-(2-Ethoxycarbonylmethoxy-phenyl)-allylidene]-4-oxo-2-thioxo-thiazolidin-3-yl}-propionic acid
167. 2-[5-(8-Carboxy-naphthalen-1-ylmethylene)-4-oxo-2-thioxo-thiazolidin-3-yl]-pentanedicarboxylic acid
168. [5-(3,4-Diacetoxy-benzyl)-4-oxo-2-thioxo-thiazolidin-3-yl]-acetic acid
169. {5-[3-(2-Amino-4-oxo-4H-chromen-3-yl)-allylidene]-4-oxo-2-thioxo-thiazolidin-3-yl}-acetic acid
170. 3-[5-(2-Amino-6,7-dimethyl-4-oxo-4H-chromen-3-ylmethylene)-4-oxo-2-thioxo-thiazolidin-3-yl]-propionic acid
171. 3-{5-[3-(6-Ethyl-4-oxo-4H-chromen-3-yl)-allylidene]-4-oxo-2-thioxo-thiazolidin-3-yl}-propionic acid
172. 2-[5-(6,8-Dimethyl-4-oxo-4H-chromen-3-ylmethylene)-4-oxo-2-thioxo-thiazolidin-3-yl]-pentanedicarboxylic acid
173. Methyl 2-(3-carboxymethyl-4-oxo-2-thioxo-thiazolidin-5-ylmethyl)-benzoate
174. Methyl 3-[3-(3-carboxymethyl-4-oxo-2-thioxo-thiazolidin-5-yliden)-propenyl]-1H-indole-6-carboxylate
175. 3-{5-[3-(4-Acetoxy-3-methoxy-phenyl)-allylidene]-4-oxo-2-thioxo-thiazolidin-3-yl}-propionic acid
176. 3-[4-Oxo-5-(3-phenyl-but-2-enylidene)-2-thioxo-thiazolidin-3-yl]-propionic acid
177. 2-[4-Oxo-2-thioxo-5-(1-#p!-tolyl-ethylidene)-thiazolidin-3-yl]-pentane-dicarboxylic acid
178. {5-[1-(4-Methoxy-phenyl)-ethylidene]-4-oxo-2-thioxo-thiazolidin-3-yl}-acetic acid
179. {5-[1-(3,4-Dichloro-phenyl)-ethyl]-4-oxo-2-thioxo-thiazolidin-3-yl}-acetic acid
180. [4-Oxo-5-(3-thiophen-2-yl-but-2-enylidene)-2-thioxo-thiazolidin-3-yl]-acetic acid
181. 3-[4-Oxo-5-(11-oxo-6,11-dihydro-dibenzo[b,e]oxepin-3-ylmethylene)-2-thioxo-thiazolidin-3-yl]-propionic acid
182. 3-{5-[3-(3,5-Dihydroxy-phenyl)-but-2-enylidene]-4-oxo-2-thioxo-thiazolidin-3-yl}-propionic acid
183. 2-[5-(4-Hydroxy-3-methoxy-benzylidene)-4-oxo-2-thioxo-thiazolidin-3-yl]-succinic acid
184. 2-[5-(4-Methyl-benzylidene)-4-oxo-2-thioxo-thiazolidin-3-yl]-succinic acid
185. 2-(4-Oxo-5-phenthylidene-2-thioxo-thiazolidin-3-yl)-succinic acid
186. 2-[5-(2,3-Dihydro-benzo[1,4]dioxin-6-ylmethylene)-4-oxo-2-thioxo-thiazolidin-3-yl]-succinic acid
187. 2-[4-Oxo-5-(4-styryl-benzylidene)-2-thioxo-thiazolidin-3-yl]-succinic acid
188. 2-[5-(4-Allyloxy-benzylidene)-4-oxo-2-thioxo-thiazolidin-3-yl]-succinic acid
189. 2-[4-Oxo-5-(4-pyrrolidin-1-yl-benzylidene)-2-thioxo-thiazolidin-3-yl]-succinic acid
190. 2-[5-(3,5-Dihydroxy-benzylidene)-4-oxo-2-thioxo-thiazolidin-3-yl]-succinic acid
191. 2-{5-[3-(4-Methoxy-phenyl)-allylidene]-4-oxo-2-thioxo-thiazolidin-3-yl}-succinic acid
192. 2-[4-Oxo-5-(4-propyl-benzylidene)-2-thioxo-thiazolidin-3-yl]-succinic acid
193. 2-[5-(2-Ethoxy-naphthalen-1-ylmethylene)-4-oxo-2-thioxo-thiazolidin-3-yl]-succinic acid
194. 2-[5-(3-Furan-2-yl-2-methyl-allylidene)-4-oxo-2-thioxo-thiazolidin-3-yl]-succinic acid
195. 2-{5-[3-(4-Hydroxy-3-methoxy-phenyl)-allylidene]-4-oxo-2-thioxo-thiazolidin-3-yl}-succinic acid
196. 2-{5-[3-(4-tert-Butyl-phenyl)-2-methyl-allylidene]-4-oxo-2-thioxo-thiazolidin-3-yl}-succinic acid
197. 2-{5-[3-(2-Hydroxy-ethoxy)-benzylidene]-4-oxo-2-thioxo-thiazolidin-3-yl}-succinic acid
198. 2-{5-[3-(4-Hydroxy-3,5-dimethoxy-phenyl)-allylidene]-4-oxo-2-thioxo-thiazolidin-3-yl}-succinic acid
199. 2-[5-(3-Benzo[b]thiophen-2-yl-allylidene)-4-oxo-2-thioxo-thiazolidin-3-yl]-succinic acid
200. 2-[5-(2,4-Bis-benzyloxy-benzylidene)-4-oxo-2-thioxo-thiazolidin-3-yl]-succinic acid
201. 2-(4-Oxo-5-pyridin-2-ylmethylene-2-thioxo-thiazolidin-3-yl)-succinic acid
202. 2-[5-(4-Benzyloxy-3,5-dimethoxy-benzylidene)-4-oxo-2-thioxo-thiazolidin-3-yl]-succinic acid
203. 2-[5-(3-Biphenyl-4-yl-allylidene)-4-oxo-2-thioxo-thiazolidin-3-yl]-succinic acid
204. 2-[5-(3-Carboxy-4-hydroxy-benzylidene)-4-oxo-2-thioxo-thiazolidin-3-yl]-succinic acid
205. 2-[5-(4-Carboxymethoxy-benzylidene)-4-oxo-2-thioxo-thiazolidin-3-yl]-succinic acid
206. 2-[5-(6-Methyl-4-oxo-4H-chromen-3-ylmethylene)-4-oxo-2-thioxo-thiazolidin-3-yl]-succinic acid
207. 2-[5-(6-Isopropyl-4-oxo-4H-chromen-3-ylmethylene)-4-oxo-2-thioxo-thiazolidin-3-yl]-succinic acid
208. 2-{5-[1-(4-Methoxy-phenyl)-ethylidene]-4-oxo-2-thioxo-thiazolidin-3-yl}-succinic acid The following Examples show some process variants which can be used for the synthesis of the compounds in accordance with the invention. However, they are not intended to be a limitation of the object of the invention. The structure of the compounds was proven by $^1$H- and, where necessary, by $^{13}$C-NMR spectroscopy. The purity of the substances was determined by C, H, N, P analysis as well as by thin-layer chromatography.

EXAMPLE 1

General Process A 5 mmol of aldehyde of the formula R—CO, wherein R has the significance given above, and 5 mmol of 4-oxo-2-thioxo-thiazolidin-3-ylcarboxylic acid derivative are heated at reflux for 10 hours together with 15 mmol of sodium acetate and 15 ml of glacial acetic acid. After cooling, the mixture is poured into H₂O. The precipitate is filtered off under suction, rinsed with H₂O and dried. For purification, it is chromatographed over silica gel with ethyl acetate:heptane (2:1).

The preparation of 2-(4-oxo-2-thioxo-thiazolidin-3-yl)-glutaric acid and 2-(4-oxo-2-thioxo-thiaolidin-3-yl)-succinic acid is effected according to Chem. Heterocycl. Compd. EN 3 528–30 (1967).

2-(5-Benzo[b]thiophen-2-ylmethylene-4-oxo-2-thioxo-thiazolidin-3-yl)-succinic acid (1)
Yellow crystals; m.p. 240° C. (dec.)
2-(5-Benzo[b]thiophen-2-ylmethylene-4-oxo-2-thioxo-thiazolidin-3-yl)-pentanedioic acid (2)
Yellow crystals; m.p. 220–1° C.
2-[5-(3,5-Di-tert-butyl-4-hydroxy-benzylidene)-4-oxo-2-thioxo-thiazolidin-3-yl]-3-phenyl-propionic acid (3)
Yellow crystals; m.p. 160° C. (dec.)
2-[5-(3,5-Di-tert-butyl-4-hydroxy-benzylidene)-4-oxo-2-thioxo-thiazolidin-3-yl]-3-(1H-indol-3-yl)-propionic acid (4)
Orange crystals; m.p. 140° C. (dec.)
[5-(5-Acetylamino-benzo[b]thiophen-2-ylmethylene)-4-oxo-2-thioxo-thiazolidin-3-yl]-acetic acid (5)
Yellow crystals; m.p. >240° C.
5-[3-(4Methoxy-2,5-dimethyl-phenyl)-allyliden]-4-oxo-2-thioxo-thiazolidin-3-yl-acetic acid (6)
Red crystals; m.p. >240° C.
5-[3-(3,5-Di-tert-butyl-4hydroxy-phenyl)-allylidene]-4-oxo-2-thioxo-thiazolidin-3-yl-acetic acid (7)
Yellow crystals; m.p. >240° C.
[5-(2,3-Dihydro-benzofuran-5-ylmethylene)-4-oxo-2-thioxo-thiazolidin-3-yl]-acetic acid (8)
Yellow crystals; m.p. 246–7° C.
(4-Oxo-5-thiophen-2-ylmethylene-2-thioxo-thiazolidin-3-yl)-acetic acid (9)
Yellow crystals; m.p. 237–9° C.
(5-Benzo[b]thiophen-2-ylmethylene-4-oxo-2-thioxo-thiazolidin-3-yl)-acetic acid (10)
Yellow crystals; m.p. 292–4° C.
[5-(3-Naphthalen-2-yl-allylidene)-4-oxo-2-thioxo-thiazolidin-3-yl]-acetic acid (11)
Orange crystals; 275–7° C.
[5-(4-Methoxy-benzylidene)-4-oxo-2-thioxo-thiazolidin-3-yl]-acetic acid (12)
Yellow crystals; m.p. 244–6° C.
[5-(5-Benzo[b]thiophen-2-yl-penta-2,4-dienylidene)-4-oxo-2-thioxo-thiazolidin-3-yl]-acetic acid (13)
Red crystals; m.p. >240° C.
[5-(4-Hydroxy-benzylidene)-4-oxo-2-thioxo-thiazolidin-3-yl]-acetic acid (14)
Yellow crystals; m.p. 230–2° C.
[5-(4-Methoxy-2,5-dimethyl-benzylidene)-4-oxo-2-thioxo-thiazolidin-3-yl]-acetic acid (15)
Yellow crystals; m.p. 240° C.
[5-(3-Benzo[b]thiophen-2-yl-allylidene)-4-oxo-2-thioxo-thiazolidin-3-yl]-acetic acid (16)
Orange crystals; m.p. >240° C.
[5-(4-Methoxy-3-methyl-benzylidene)-4-oxo-2-thioxo-thiazolidin-3-yl]-acetic acid (17)
Yellow crystals; m.p. 235–6° C.
2-[5-(3,5-Di-tert-butyl-4-hydroxy-benzylidene)-4-oxo-2-thioxo-thiazolidin-3-yl]-pentanedioic acid (18)
Yellow crystals; m.p. 130° C. (dec.)
[5-(4Benzyloxy-3,5-dimethoxy-benzylidene)-4-oxo-2-thioxo-thiazolidin-3-yl]-acetic acid (19)
M.p. 128–30° C.
[5-(3,4-Bis-benzyloxy-benzylidene)-4-oxo-2-thioxo-thiazolidin-3-yl]-acetic acid (20)
Yellow crystals; m.p. 187–8° C.
[5-(3-Biphenyl-4-yl-allylidene)-4-oxo-2-thioxo-thiazolidin-3-yl]-acetic acid (21)
Orange crystals; m.p. 130° C. (dec.)
5-[1-Methyl-3-(2,6,6-trimethyl-cyclohex-1-enyl)-allylidene]-4-oxo-2-thioxo-thiazolidin-3-yl-acetic acid (22)
Brown crystals; m.p. 100° C. (dec.)
[5-(3-tert-Butyl-4-hydroxy-benzylidene)-4-oxo-2-thioxo-thiazolidin-3-yl]-acetic acid (23)
Yellow crystals; m.p. >240° C.
2-[5-(3,5-Di-tert-butyl-4-hydroxy-benzylidene)-4-oxo-2-thioxo-thiazolidin-3-yl]-succinic acid (24)
Brown crystals; m.p. 240° C. (dec.)
[5-(3,5-Di-tert-butyl-4-hydroxy-benzylidene)-4-oxo-2-thioxo-thiazolidin-3-yl]-acetic acid (25)
Orange crystals; m.p. 120–1° C.
[5-(4-Benzyloxy-benzylidene)-4-oxo-2-thioxo-thiazolidin-3-yl]-acetic acid (26)
Yellow crystals; m.p. 205–6° C.
5-[1-(3,5-Dihydroxy-phenyl)-ethylidene]-4-oxo-2-thioxo-thiazolidin-3-yl-acetic acid (27)
Yellow crystals; m.p. 184–8° C.
5-[1-(4Carboxymethoxy-phenyl)-ethylidene]-4-oxo-2-thioxo-thiazolidin-3-yl-acetic acid (28)
Yellow crystals; m.p. 111–20° C. (dec.)
[4-Oxo-2-thioxo-5-(2,3,4-trihydroxy-benzylidene)-thiazolidin-3-yl]-acetic acid (29)
Ochre-coloured crystals; m.p. 263° C. (dec.)
[5-(2-Hydroxy-4,6-dimethoxy-benzylidene)-4-oxo-2-thioxo-thiazolidin-3-yl]-acetic acid (30)
Pale brown crystals; m.p. 194° C. (dec.)
[5-(3-Benzyloxy-benzylidene)-4-oxo-2-thioxo-thiazolidin-3-yl]-acetic acid (31)
Yellow crystals; m.p. 178–81° C.
3-[5-(4-Benzyloxy-benzylidene)-4-oxo-2-thioxo-thiazolidin-3-yl]-propionic acid (32)
Yellow crystals; m.p. 188–91° C.
2-[5-(4-Benzyloxy-benzylidene)-4-oxo-2-thioxo-thiazolidin-3-yl]-propionic acid (33)
Yellow crystals; m.p. 125–8° C.
[5-(5-Benzyloxy-2-hydroxy-benzylidene)-4-oxo-2-thioxo-thiazolidin-3-yl]-acetic acid (34)
Orange crystals; m.p. 130–3° C.
5-[4-(4-Methoxy-benzyloxy)-benzylidene]-4-oxo-2-thioxo-thiazolidin-3-yl-acetic acid (35)
Yellow crystals; m.p. 172–3° C.
5-[4-(Benzo[1,3]dioxol-5-ylmethoxy)-benzylidene]-4-oxo-2-thioxo-thiazolidin-3-yl-acetic acid (36)
Yellow crystals; m.p. 206–7° C.
5-[4-Oxo-2-thioxo-5-(3,4,5-trihydroxy-benzylidene)-thiazolidin-3-yl]-pentanecarboxylic acid (37)
m.p. 212–4° C.
5-[4-(3-Methoxy-benzyloxy)-benzylidene]-4-oxo-2-thioxo-thiazolidin-3-yl-acetic acid (38)
Yellow crystals; m.p. 191–3° C.
[5-(4-Hydroxy-3,5-dimethyl-benzylidene)-4-oxo-2-thioxoidin-3-yl]-acetic acid (39)
Orange crystals; m.p. 277–9° C.
[5-(4-Benzyloxy-3,5-dihydroxy-benzylidene)-4-oxo-2-thioxo-thiazolidin-3-yl]-acetic acid (40)
M.p. 178–80° C.
[5-(2,5-Bis-benzyloxy-benzylidene)-4-oxo-2-thioxo-thiazolidin-3-yl]-acetic acid (41)
Yellow crystals; m.p. 196–8° C.

[4-Oxo-2-thioxo-5-(3,4,5-triacetoxy-benzylidene)-thiazolidin-3-yl]-acetic acid (42)
Orange crystals; m.p. 200° C. (dec.)

5-[3-(5,6-Diethoxy-benzo[b]thiophen-2-yl)-allylidene]-4-oxo-2-thioxo-thiazolidin-3-yl-acetic acid (43)
Red crystals; m.p. 252–3° C.

(5-Cyclohex-3-enylmethylene-4-oxo-2-thioxo-thiazolidin-3-yl)-acetic acid (44)
Beige crystals; m.p. 180–2° C.

[4-Oxo-5-(3-phenyl-propylidene)-2-thioxo-thiazolidin-3-yl]-acetic acid (45)
Orange crystals; m.p. 108–11° C.

5-[3-Methyl-5-(2,6,6-trimethyl-cyclohex-1-enyl)-penta-2,4-dienyliden]-4-oxo-2-thioxo-thiazolidin-3-yl-acetic acid (46)
Orange crystals; m.p. 153–5° C.

5-(3,5-Di-tert-butyl-hydroxy-benzylidene)-3-methyl-2-thioxo-thiazolidin-4-one (47)
Yellow crystals; m.p. >240° C.

Methyl [5-(3,5-Di-tert-butyl-4-hydroxy-benzylidene)-4-oxo-2-thioxo-thiazolidin-3-yl]-acetate (48)
Yellow crystals; m.p. 165–70° C.

2-[5-(3,5-Di-tert-butyl-4-hydroxy-benzylidene)-4-oxo-2-thioxo-thiazolidin-3-yl]-N,N-diethyl-acetamide (49)
Yellow crystals; m.p. 223–5° C.

Methyl 5-[3-(5,6-diethoxy-benzo[b]thiophen-2-yl)-allylidene]-4-oxo-2-thioxo-thiazolidin-3-yl-acetate (50)
Violet crystals; m.p. 211–5° C.

2-5-[3-(5,6-Diethoxy-benzo[b]thiophen-2-yl)-allylidene]-4-oxo-2-thioxo-thiazolidin-3-yl-N,N-diethyl-acetamide (51)
Red crystals; m.p. 210–2° C.

Benzyl 4-(3-carboxymethyl-4-oxo-2-thioxo-thiazolidin-5-ylidenmethyl)-piperidine-1-carboxylate (52)
Yellow crystals; m.p. 114–5° C.

5-[3,7-Dimethyl-9-(2,6,6-trimethyl-cyclohex-1-enyl)-nona-2,4,6,8-tetraenylidene]-4-oxo-2-thioxo-thiazolidin-3-yl-acetic acid (53)
Black (sic) crystals; m.p. 144° C. (dec.)

[5-(3,4-Dihydroxy-2,5-dimethyl-benzylidene)-4-oxo-2-thioxo-thiazolidin-3-yl]-acetic acid (54)
Yellow crystals; m.p. >240° C.

[5-(3,4-Diethoxy-2,5-dimethyl-benzylidene)-4-oxo-2-thioxo-thiazolidin-3-yl]-acetic acid (55)
Ochre coloured crystals; m.p. 185–90° C.

5-[3-(3,4-Diethoxy-2,5-dimethyl-phenyl)-allylidene]-4-oxo-2-thioxo-thiazolidin-3-yl-acetic acid (56)
Green crystals; m.p. 210° C. (dec.)

5-[5-Methyl-7-(2,6,6-trimethyl-cyclohex-1-enyl)-hepta-2,4,6-trienyliden]-4-oxo-2-thioxo-thiazolidin-3-yl-acetic acid (57)
Black crystals; m.p. 192–5° C.

3-(5-Benzo[1,3]dioxol-5-ylmethylene-4-oxo-2-thioxo-thiazolidin-3-yl)-propionic acid (58)
Yellow crystals; m.p. 174–6° C.

3-[4-Oxo-2-thioxo-5-(2,6,6-trimethyl-cyclohex-1-enylmethylene)-thiazolidin-3-yl]-propionic acid (59)
Yellow-orange crystals; m.p. 166–8° C.

3-[5-(3,5-Di-tert-butyl-4-hydroxy-benzylidene)-4-oxo-2-thioxo-thiazolidin-3-yl]-propionic acid (60)
Yellow crystals; m.p. 218–9° C.

3-(5-Naphthalen-1-ylmethylene-4-oxo-2-thioxo-thiazolidin-3-yl)-propionic acid (61)
Orange crystals; m.p. 159–61° C.

3-[5-(3-Benzo[b]thiophen-2-yl-allylidene)-4-oxo-2-thioxo-thiazolidin-3-yl]-propionic acid (62)
Orange crystals; m.p. 246–8° C.

[5-(4-Dibutylamino-benzylidene)-4-oxo-2-thioxo-thiazolidin-3-yl]-acetic acid (63)
Orange crystals; m.p. 186–8° C.

[4-Oxo-5-(4-pentyl-benzylidene)-2-thioxo-thiazolidin-3-yl]-acetic acid (64)
Yellow crystals; m.p. 160≠2° C.

[5-(3-Methoxy-benzylidene)-4-oxo-2-thioxo-thiazolidin-3-yl]-acetic acid (65)
Yellow crystals; m.p. 193–6° C.

[4-Oxo-2-thioxo-5-(2,4,5-triethyl-benzylidene)-thiazolidin-3-yl]-acetic acid (66)
Yellow crystals; m.p. 234–6° C.

[5-(2-Hexyloxy-benzylidene)-4-oxo-2-thioxo-thiazolidin-3-yl]-acetic acid (67)
Yellow crystals; m.p. 148–50° C.

[5-(4-Methyl-benzylidene)-4-oxo-2-thioxo-thiazolidin-3-yl]-acetic acid (68)
Yellow crystals; m.p. 234–6° C.

[5-(4-Methoxy-2,3-dimethyl-benzylidene)-4-oxo-2-thioxo-thiazolidin-3-yl]-acetic acid (69)
Yellow crystals; m.p. 215–7° C.

[5-(4-Hydroxy-3,5-dimethoxy-benzylidene)-4-oxo-2-thioxo-thiazolidin-3-yl]-acetic acid (70)
Orange crystals; m.p. 238–40° C.

5-(3-Carboxymethyl-4-oxo-2-thioxo-thiazolidin-5-ylidenmethyl)-2-hydroxy-benzoic acid (71)
Yellow crystals; m.p. >260° C.

3-5-[1-Methyl-3-(2,6,6-trimethyl-cyclohex-1-enyl)-allylidene]-4-oxo-2-thioxo-thiazolidin-3-yl-propionic acid (72)
Orange crystals; m.p. 160–1° C.

[5-(1,4-Dihydroxy-10-methoxy-5,8-dimethyl-3,7-dioxo-1,3-dihydro-7H-benzo[e]furo[3',4':3,4]benzo[b][1,4]dioxepin-11-ylmethylene)-4-oxo-2-thioxo-thiazolidin-3-yl]-acetic acid (73)
Dark green crystals; m.p. >260° C.

[5-(2-Methyl-1H-indol-3-ylmethylene)-4-oxo-2-thioxo-thiazolidin-3-yl]-acetic acid (74)
Brown crystals; m.p. 268–70° C.

[5-(3,4-Diacetoxy-benzylidene)-4-oxo-2-thioxo-thiazolidin-3-yl]-acetic acid (75)
Yellow crystals; m.p. 193–5° C.

EXAMPLE 2

Compounds of general formula (I) were investigated in a suitable assay for the capability of stimulating cyclic adenylate cyclase.

TABLE I

| Example No. | Name | % cAMP (Test conc. 50 μM) |
|---|---|---|
| 3 | 2-[5-(3,5-Di-tert-butyl-4-hydroxy-benzylidene)-4-oxo-2-thioxo-thiazolidin-3-yl]-3-phenyl-propionic acid | 8 |
| 13 | [5-(5-Benzo[b]thiophen-2-yl-penta-2,4-dienylidene)-4-oxo-2-thioxo-thiazolidin-3-yl]-acetic acid | 10 |
| 16 | [5-(3-Benzo[b]thiophen-2-yl-allylidene)-4-oxo-2-thioxo-thiazolidin-3-yl]-acetic acid | 8 |
| 22 | 5-[1-Methyl-3-(2,6,6-trimethyl-cyclohex-1-enyl)-allylidene]-4-oxo-2-thioxo-thiazolidin-3-yl-acetic acid | 10 |
| 23 | [5-(3-tert-Butyl-4-hydroxy-benzylidene)-4-oxo-2-thioxo-thiazolidin-3-yl]-acetic acid | 8 |
| 25 | [5-(3,5-Di-tert-butyl-4-hydroxy-benzylidene)-4-oxo-2-thioxo-thiazolidin-3-yl]-acetic acid | 40 |

TABLE I-continued

| Example No. | Name | % cAMP (Test conc. 50 μM) |
|---|---|---|
| 46 | 5-[3-Methyl-5-(2,6,6-trimethyl-cyclohex-1-enyl)-penta-2,4-dienylidene]-4-oxo-2-thioxo-thiazolidin-3-yl-acetic acid | 30 |
| 59 | 3-[4-Oxo-2-thioxo-5-(2,6,6-trimethyl-cyclohex-1-enylmethylene)-thiazolidin-3-yl]-propionic acid | 15 |
| 60 | 3-[5-(3,5-Di-tert-butyl-4-hydroxy-benzylidene)-4-oxo-2-thioxo-thiazolidin-3-yl]-propionic acid | 20 |
| 72 | 3-5-[1-Methyl-3-(2,6,6-trimethyl-cyclohex-1-enyl)-allylidene]-4-oxo-2-thioxo-thiazolidin-3-yl-propionic acid | 15 |

What is claimed is:

1. A method of treating a metabolic bone disorder in a subject in need of such treatment comprising administering to said subject an effective amount of a compound of general formula (I)

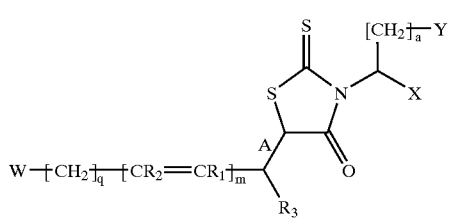

(I)

in which
- m signifies a number between 0–8, and
- q signifies a number between 0–8, wherein m and q are not both 0,
- a signifies a number between 0–4,
- A signifies a single or double bond,
- $R_1,R_2$ signify hydrogen or lower alkyl, whereby $R_1,R_2$ are the same or different and, when m signifies 2–8, $R_1$ and $R_2$ in the group $CR_1=CR_2$ optionally have various significances within the following sequence,
- $R_3$ signifies hydrogen or lower alkyl,
- X signifies hydrogen or —$(CH_2)_b$—$COR_4$ with b=0–4,
- Y signifies hydrogen, —$COR_4$, phenyl or indolyl residue
- $R_4$ signifies hydroxyl, lower alkoxy or the $NR_1R_2$ residue, whereby $R_1$ and $R_2$ are the same or different, and
- W signifies an optionally mono- or polysubstituted saturated or unsaturated mono-, bi- or tricycle which optionally contain one or more hetero atoms, wherein W is not phenyl or indolyl, if m and a are both 0, $R_3$ is hydrogen and A is a double bond, or a physiologically compatible salt, ester, optically active form, racemate, tautomer or prodrug thereof.

2. The method of claim 1 wherein the compound of general formula (I) is in admixture with usual pharmaceutical adjuvants and carrier material.

3. A method of treatment or prevention of metabolic bone disorders in a patient in need of such treatment or prevention, comprising administering an effective amount of a compound of general formula (I)

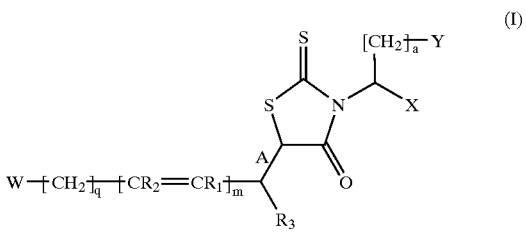

(I)

in which
- m signifies a number between 0–8 and q signifies a number between 0–8, wherein m and q are not both 0,
- a signifies a number between 0–4,
- A signifies a single or double bond,
- $R_1,R_2$ signify hydrogen or lower alkyl, wherein $R_1$ and $R_4$ are the same or different,
- $R_3$ signifies hydrogen or lower alkyl,
- X signifies hydrogen or —$(CH_2)_b$—$COR_4$ with b=0–4,
- Y signifies —$COR_4$, phenyl or indolyl,
- $R_4$ signifies hydroxyl, lower alkoxy or —$NR_1R_2$, whereby $R_1$ and $R_2$ are the same or different, and
- W signifies an optionally mono- or polysubstituted saturated or unsaturated monocycle, bicycle or tricycle which optionally contains one or more hetero atoms, with the proviso that if W is a substituted phenyl, the substituent is selected from the group consisting of lower alkyl, alkoxy, alkoxycarbonylalkyl, alkoxycarbonyl, acetylamino, alkoxydialkylamino, amino, dialkylamino, benzyl, benzyloxy, benzyloxybenzyloxy, carboxyl, chlorophenylsulphonyl, dioxymethylene, mercaptoalkyl, nitro, phenoxy, styryl and halogen.

* * * * *